US00PP15556P2

(12) United States Plant Patent
Boeder

(10) Patent No.: US PP15,556 P2
(45) Date of Patent: Feb. 15, 2005

(54) ***CHRYSANTHEMUM* PLANT NAMED 'HERCULES'**

(50) Latin Name: *Chrysanthemum morifolium*
Varietal Denomination: Hercules

(75) Inventor: Mark Roland Boeder, The Hague (NL)

(73) Assignee: Chrysanthemum Breeders Association, N.v. (NL)

( * ) Notice: Subject to any disclaimer, the term of this patent is extended or adjusted under 35 U.S.C. 154(b) by 18 days.

(21) Appl. No.: 10/756,300

(22) Filed: Jan. 14, 2004

(51) Int. Cl.[7] ..... A01H 5/00
(52) U.S. Cl. ..... Plt./293
(58) Field of Search ..... Plt./293

*Primary Examiner*—Bruce R. Campell
*Assistant Examiner*—S. B. McCormick-Ewoldt
(74) *Attorney, Agent, or Firm*—Parkhurst & Wendel, L.L.P.

(57) ABSTRACT

A *chyrsanthemum* plant named 'Hercules' characterized by its medium sized blooms with red ray florets and prolific branching; natural season flower date August 18–23; blooming for a period of 5 weeks.

2 Drawing Sheets

BACKGROUND OF THE INVENTION

'Hercules' is a product of a breeding and selection program for outdoor pot mums (garden mums) which had the objective of creating new *chrysanthemum* cultivars with a decorative type flower, a natural season flower date around August 18–23; blooming for a period of 5 weeks. The new plant of the present invention comprises a new and distinct cultivar of *Chrysanthemum* plant 'Hercules' is a seedling resulting from the open pollination among groups of *chrysanthemum* cultivars maintained under the control of the inventor for breeding purposes. The new and distinct cultivar was discovered and selected as one flowering plant by Mark Roland Boeder on a cultivated field in Rijsenhout Holland in August 2001. The seedling resulted from the crossing of the female parent, 22.0296, with a mixed population of *chrysanthemum* plants serving as male parents. The plant has been asexually reproduced by cuttings in greenhouses at Rijsenhout Holland. The new cultivar has been found to retain its distinctive characteristics through successive propagations.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
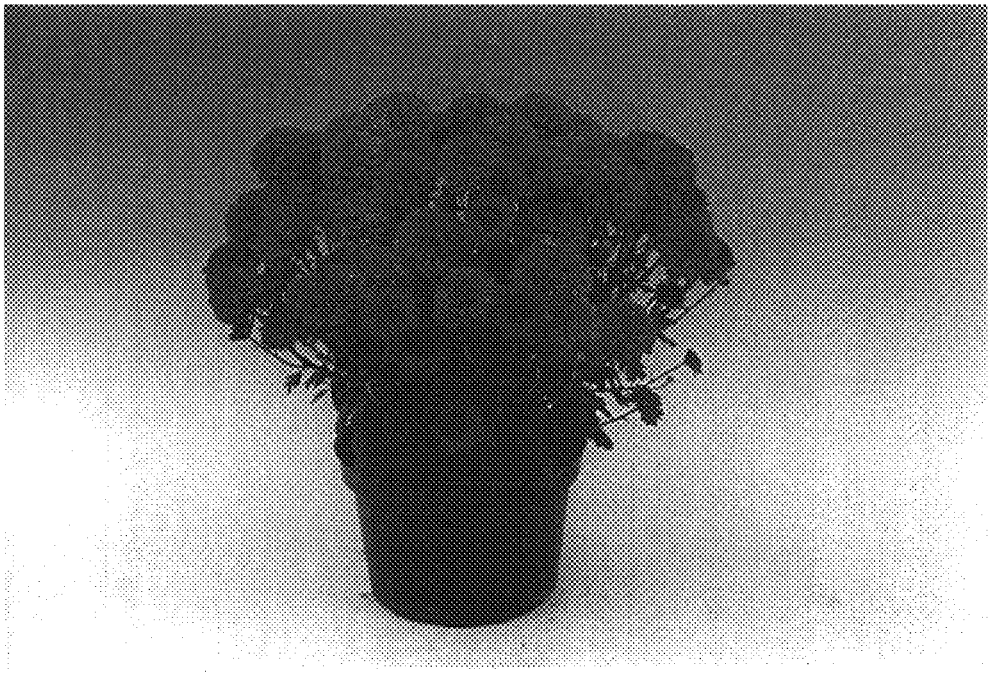
FIG. 1 shows a plant of the cultivar in full bloom.
Figure 2:
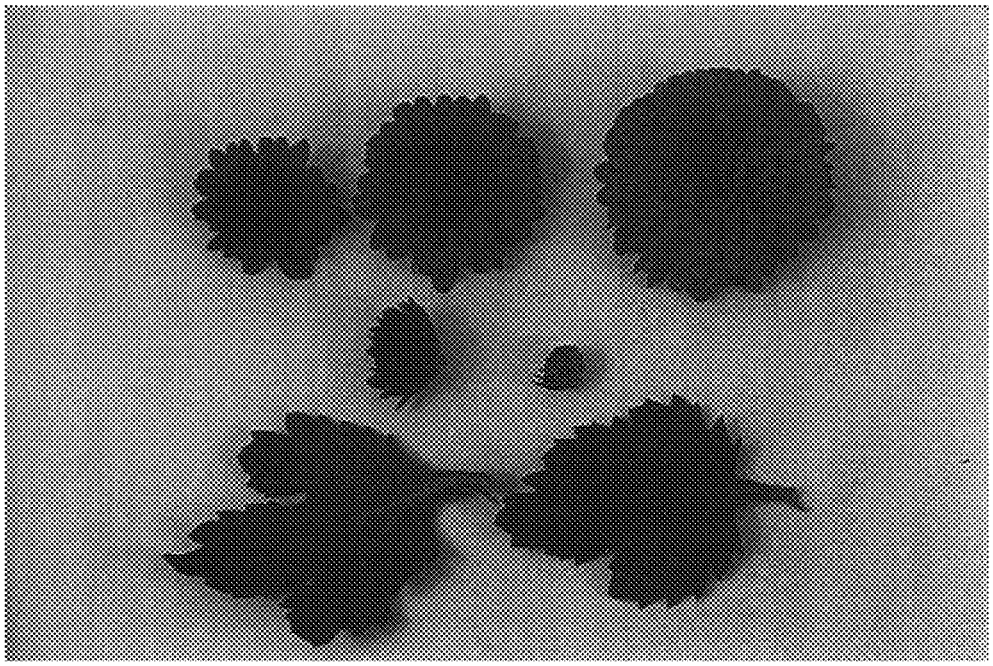
FIG. 2 shows the various stages of bloom and foliage of the new cultivar.

This new variety of *chrysanthemum* is of the botanical classification *Chrysanthemum morifolium.* The observations and measurements were gathered from plants grown out door in Rijsenhout, Holland under natural day length and temperature and planted in week 23 in 2002. The natural blooming date of this crop was August 18–23 (week 34). The average height of the plants was 30 cms. No growth retardants were used. No tests were done on disease or insect resistance or susceptibility. No tests were done on cold or drought tolerance. This new variety produces medium sized blooms with red ray florets blooming for a period of 5 weeks.

From the cultivars known to inventor the most similar existing cultivar in comparison to 'Hercules' is 'Dark Grenadine' (U.S. Plant Pat. No. 7,632). When 'Dark Grenadine' and 'Hercules' are being compared the following differences are noticed: The differences of 'Dark Grenadine' and 'Hercules' are (1) Flower size. The flowers of 'Dark Grenadine' are larger in size than those of 'Hercules' (2) Color ray florets. The ray florets of 'Dark Grenadine' are less red than 'Hercules'.

The following is a description of the plant and characteristics that distinguish 'Hercules' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 1995.

TABLE 1

Botanical Description of cultivar 'Hercules'

| | |
|---|---|
| Bud | |
| Size | Small; cross-section 1 cm, height 1 cm |
| Outside color | Yellow-green 147D |
| Involucral bracts | 2 rows, length 7 mm, width 3 mm |
| Involucral bracts among disc-florets | Not present |
| Involucral bracts color | Green 138A |
| Bloom | |
| Type | Decorative |
| Size | Medium |
| Fully expanded | 5 cm |
| Peduncle length | 5 cm |
| Peduncle color | Yellow-green 148B |
| Number of blooms per branch | Approx. 12 blooms per branch |
| Performance on the plant | 5 weeks |
| Seeds | Produced in small quantities, ovate grey-brown 199A, 1½ mm in length. |
| Fragrance | Typical *chrysanthemum,* slightly |

TABLE 1-continued

| Botanical Description of cultivar 'Hercules' | |
|---|---|
| Color | |
| Center of the flower | Immature Red 46A<br>Mature Red 46A |
| Color of upper surface of the ray-florets | Red 46C |
| Color of the lower surface of the ray-florets | Orange-red 34C |
| Tonality from distance | A garden mum with red flowers |
| Color of ray florets after aging of the flowers | Red 46D |
| Ray florets | |
| Texture | Upper and under side smooth |
| Number | 250 |
| Cross-section | Flat |
| Longitudinal axis of majority | Straight |
| Length of corolla tube | 0.2 cm |
| Ray-floret margin | Entire |
| Ray-floret length | 2 cm |
| Ray-floret width | 0.6 cm |
| Ratio length/width | Medium |
| Shape of tip | Rounded |
| Disc florets | Absent |
| Receptacle shape | Domed raised |
| Reproductive Organs | |
| Stamen | Absent |
| Pollen | Not produced |
| Styles | Thick |
| Style color | Yellow 13A |
| Style length | 4 mm |
| Stigma color | Yellow-green 144A |
| Stigma width | 1 mm |
| Ovaries | Enclosed in calyx |
| Plant | |
| Form | A garden mum outdoor mounded and round |
| Growth habit | Compact and spreading |
| Growth rate | Strong |
| Height | 30 cm |
| Width | 40 cm |
| Stem color | Yellow-green 148A with streaks of Greyed-red 181C |
| Stem strength | Strong |
| Stem brittleness | Not brittle |
| Stem anthocyanin Coloration | Present |
| Internode length | 2.5 cm |

TABLE 1-continued

| Botanical Description of cultivar 'Hercules' | |
|---|---|
| Length of lateral branch | From top to bottom 19 cm |
| Lateral branch color | Yellow-green 148A |
| Lateral branch, attachment | Strong |
| Branching (average number of lateral branches) | Good with 10 breaks after pinching |
| Natural season blooming date | August 18–23 |
| Foliage | |
| Leaf color | Upper side Yellow-green 147A<br>Under side Green 138B |
| Color midvein | Upper side Green 138C<br>Under side Yellow-green 148C |
| Size | Medium; length 5.5 cm, width 3.3 cm |
| Quantity (number per lateral branch) | 15–18 |
| Shape | Cordiform |
| Texture upper side | Glabrous |
| Texture under side | Pubescent |
| Venation arrangement | Palmate |
| Shape of the margin | Serrated |
| Shape of base of sinus Between lateral lobes | Rounded |
| Margin of sinus between lateral lobes | Diverging |
| Shape of base | Obtuse |
| Apex | Mucronate |
| Petiole length | 1 cm |
| Petiole color | Green 138C |

TABLE 2

| Differences with the comparison variery | | |
|---|---|---|
| | 'Hercules' | 'Dark Grenadine' |
| Flower size | 5 cm | 7 cm |
| Color ray florets | Red 46C | Greyed-red 179A |

I claim:

1. A new and distinct variety of *chrysanthemum* plant as described and illustrated.

* * * * *